US006767542B2

(12) United States Patent
Paterson et al.

(10) Patent No.: US 6,767,542 B2
(45) Date of Patent: Jul. 27, 2004

(54) COMPOSITIONS AND METHODS FOR ENHANCING IMMUNOGENICITY OF ANTIGENS

(75) Inventors: Yvonne Paterson, Philadelphia, PA (US); George Raymond Gunn, III, Glenside, PA (US); Christian Peters, Radnor, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 76 days.

(21) Appl. No.: 09/735,450

(22) Filed: Dec. 13, 2000

(65) Prior Publication Data

US 2002/0025323 A1 Feb. 28, 2002

Related U.S. Application Data

(63) Continuation-in-part of application No. 09/537,642, filed on Mar. 29, 2000.
(51) Int. Cl.$^7$ .................. A61K 39/02; A61K 39/09; A61K 39/295; A61K 39/385
(52) U.S. Cl. .................. 424/192.1; 424/190.1; 424/193.1
(58) Field of Search .................. 424/190.1, 192.1, 424/193.1, 200.1

(56) References Cited

U.S. PATENT DOCUMENTS 5,830,702 A 11/1998 Portnoy et al.
6,051,237 A * 4/2000 Paterson et al.

FOREIGN PATENT DOCUMENTS

WO  WO 99/10496  4/1999

OTHER PUBLICATIONS

J Immunology 146(10): 3604–3616; May 1991.*
Bielecki et al., "*Bacillus subtilis* expressing a haemolysin gene from *Listeria monocytogenes* can grow in mammalian cells", *Nature* 1990 354:175–176.

Decatur A.L. et al., "A PEST–Like Sequence in Listeriolysin O Essential for *Listeria monocytogenes* Pathogenicity", *Science* 2000 290:992–995.
Gentschev et al., "Salmonella Strain Secreting Active Listeriolysin Changes Its Intracellular Localization", *Infect. Immun.* 1995 63:4202–4205.
Ikonimidis et al., "Delivery of a Viral Antigen to the Class I Processing and Presentation Pathway by *Listeria monocytogenes*", *J. Exp. Med.* 1994 180:2209–2218.
Kaufman S.H. et al., "Impact of intracellular location of and antigen display by intracellular bacteria:implications for vaccine development", *J. Immunol. Lett.* 1999 65(1–2):81–84.
Lin et al., "Treatment of Established Tumors with a Novel Vaccine That Enhances Major Histocompatibility Class II Presentation of Tumor Antigen[1]", *Cancer Res.* 1996 56:21–26.
Pan et al., "Rsgression of Established Tumors in Mice Mediated by the Oral Administration of a Recombinant *Listeria monocytogenes* Vaccine[1]", *Cancer Res.* 1995 55:4776–4779.
Realini et al., "Proposed roles in protein–protein association and presentation of peptides by MHC Class I receptors", *FEBS Lett.* 1994 348:109–113.
Rechsteiner and Rogers, "PEST sequences and regulation by proteolysis", *TIBS* 1996 21:267–271.
Tanabe et al., "Induction of Protective T Cells against *Listeria monocytogenes* in Mice by Immunization with a Listeriolysin O–Negative Avirulent Strain of Bacteria and Liposome–Encapsulated Listeriolysin O", *Infect. Immun.* 1999 67(2):568–575.
Wu et al., "Engineering an intracellular pathway for major histocompatibility complex class II presentation of antigens", *Cancer Res.* 1996 56:21–26.

* cited by examiner

*Primary Examiner*—Christina Chan
*Assistant Examiner*—Phuong N Huynh
(74) *Attorney, Agent, or Firm*—Morgan, Lewis & Bockius, LLP

(57) ABSTRACT

Compositions and methods for enhancing the immunogenicity of an antigen via fusion to a PEST-like amino acid sequence derived from a prokaryotic organism are provided.

4 Claims, 6 Drawing Sheets

SEQUENCE LISTING

<160> NUMBER OF SEQ ID NOS: 13

<210> SEQ ID NO 1
<211> LENGTH: 32
<212> TYPE: PRT
<213> ORGANISM: Listeria monocytogenes

<400> SEQUENCE: 1

Lys Glu Asn Ser Ile Ser Ser Met Ala Pro Pro Ala Ser Pro Pro Ala
 1               5                   10                  15

Ser Pro Lys Thr Pro Ile Glu Lys Lys His Ala Asp Glu Ile Asp Lys
            20                  25                  30

<210> SEQ ID NO 2
<211> LENGTH: 14
<212> TYPE: PRT
<213> ORGANISM: Listeria monocytogenes

```
<400> SEQUENCE: 2

Lys Thr Glu Glu Gln Pro Ser Glu Val Asn Thr Gly Pro Arg
1               5                   10

<210> SEQ ID NO 3
<211> LENGTH: 28
<212> TYPE: PRT
<213> ORGANISM: Listeria monocytogenes

<400> SEQUENCE: 3

Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
            20                  25

<210> SEQ ID NO 4
<211> LENGTH: 20
<212> TYPE: PRT
<213> ORGANISM: Listeria monocytogenes

<400> SEQUENCE: 4

Lys Asn Glu Glu Val Asn Ala Ser Asp Phe Pro Pro Pro Thr Asp
1               5                   10                  15

Glu Glu Leu Arg
            20

<210> SEQ ID NO 5
<211> LENGTH: 33
<212> TYPE: PRT
<213> ORGANISM: Listeria monocytogenes

<400> SEQUENCE: 5

Arg Gly Gly Ile Pro Thr Ser Glu Glu Phe Ser Ser Leu Asn Ser Gly
1               5                   10                  15

Asp Phe Thr Asp Asp Glu Asn Ser Glu Thr Thr Glu Glu Glu Ile Asp
            20                  25                  30

Arg

<210> SEQ ID NO 6
<211> LENGTH: 17
<212> TYPE: PRT
<213> ORGANISM: Streptococcus pyogenes

<400> SEQUENCE: 6

Lys Gln Asn Thr Ala Ser Thr Glu Thr Thr Thr Thr Asn Glu Gln Pro
1               5                   10                  15

Lys

<210> SEQ ID NO 7
<211> LENGTH: 17
<212> TYPE: PRT
<213> ORGANISM: Streptococcus equisimilis

<400> SEQUENCE: 7

Lys Gln Asn Thr Ala Asn Thr Glu Thr Thr Thr Thr Asn Glu Gln Pro
1               5                   10                  15

Lys

<210> SEQ ID NO 8
<211> LENGTH: 27
```

-continued

```
<212> TYPE: DNA
<213> ORGANISM: Artificial Sequence
<220> FEATURE:
<223> OTHER INFORMATION: Description of Artificial Sequence: synthetic

<400> SEQUENCE: 8
gctagccctc ctttgattag tatattc                                      27

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: synthetic

<400> SEQUENCE: 9
gcggatgaaa tcgataagca tggagataca cctaca                            36

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: synthetic

<400> SEQUENCE: 10
cgcctacttt agctattcgt acctctatgt ggatgt                            36

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: synthetic

<400> SEQUENCE: 11
gagtctttgg tattgggccc                                              20

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: synthetic

<400> SEQUENCE: 12
gctctagatt atggtttctg ag                                           22

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: synthetic

<400> SEQUENCE: 13
ggggtaccct cctttgatta gtatat                                       26
```

COMPOSITIONS AND METHODS FOR ENHANCING IMMUNOGENICITY OF ANTIGENS

INTRODUCTION

This patent application is a continuation-in-part of U.S. application Ser. No. 09/537,642, filed Mar. 29, 2000.

This invention was supported in part by funds from the U.S. government (NIH Grant No. CA69632) and the U.S. government may therefore have certain rights in the invention.

BACKGROUND OF THE INVENTION

Stimulation of an immune response is dependent upon the presence of antigens recognized as foreign by the host immune system. Bacterial antigens such as *Salmonella enterica* and *Mycobacterium bovis* BCG remain in the phagosome and stimulate CD4 T-cells via antigen presentation through major histocompatibility class II molecules. In contrast, bacterial antigens such as *Listeria monocytogenes* exit the phagosome into the cytoplasm. The phagolysosomal escape of *L. monocytogenes* is a unique mechanism which facilitates major histocompatibility class I antigen presentation of listerial antigens. This escape is dependent upon the pore-forming sulfhydryl-activated cytolysin, listeriolysin O (LLO).

The ability of *L. monocytogenes* to break down the vacuole within a host cell and enter the cytoplasm has led to its use as a recombinant vaccine. U.S. Pat. No. 5,830,702 describes vaccines comprising attenuated mutants of Listeria spp. genetically engineered to express foreign antigens in the cytoplasm of infected macrophages and other cells. Several approaches for expressing the antigen in Listeria spp. are described including generation of a fusion protein of a selected foreign antigen and a listerial protein, preferably an enzyme involved in lysis of host vacuoles. In particular, a fusion protein encoding the hly promoter and the first 416 amino acids of LLO fused in-frame to the entire coding sequence of the NP antigen was constructed in *E.coli* and on transformation to *Listeria monocytogenes* is demonstrated to secrete a 105 kDA protein that reacts with antiserum to LLO and NP (col. 24 of '702 patent). Recombinant *L. monocytogenes* secreting a fusion protein comprising listeriolysin O and NP (LLO-NP) was demonstrated to target infected cells for lysis by NP-specific class I-restricted cytotoxic T cells. In contrast, a hemolysin-negative *L. monocytogenes* strain expressing LLO-NP presented the antigen in a class II restricted manner (Ikonimidis et al. *J. Exp. Med.* 1994 180:2209–2218). Thus, from these studies it was surmised that hemolysin-dependent bacterial escape from the vacuole is necessary for class I presentation in vitro.

The escape function of *L. monocytogenes* has also been transferred to *Bacillus subtilis* and attenuated Salmonella ssp. strains (Bielecki et al. *Nature* 1990 354:175–176, Gentschev et al. *Infect. Immun.* 1995 63:4202–4205). *S. enteric* and *M. bovis* BCG vaccine carriers which secrete listeriolysin O have also been constructed (Kaufman, S. H. and Hess, *J. Immunol. Lett.* January 1999 65(1–2):81–4). These constructs are taught to be capable of introducing antigens into the MHC class II and MHC class I pathway, resulting in stimulation of both CD4 and CD8 T-cells. Comparison of *S. enterica* vaccines which display the same listerial antigen in secreted and somatic form showed the secreted antigen display to be superior to the somatic antigen display (Kaufman, S. H. and Hess, *J. Immunol. Lett.* January 1999 65(1–2):81–4).

WO 99/10496 discloses recombinant BCG strains secreting hemolytically active hly with an improved MHC class I-restricted immune response for use as a vaccine against tuberculosis.

Administration of purified listeriolysin O encapsulated in liposomes has also been reported to be effective in the induction of antigen-specific Th1-dependent protective immunity to various kinds of intracellular parasitic bacteria in vivo (Tanabe et al. *Infect. Immun.* February 1999 67(2): 568–75).

PEST sequences in eukaryotic proteins have long been identified. It has been taught that proteins containing amino acid sequences that are rich in prolines (P), glutamic acids (E), serines (S) and threonines (T), generally, but not always, flanked by clusters containing several positively charged amino acids, have rapid intracellular half-lives (Rogers et al. *Science* 1986 234:364–369). Further, it has been shown that these sequences target the protein to the ubiquitin-proteosome pathway for degradation (Rechsteiner and Rogers TIBS 1996 21:267–271). This pathway is also used by eukaryotic cells to generate immunogenic peptides that bind to MHC class I and it has been hypothesized that PEST sequences are abundant among eukaryotic proteins that give rise to immunogenic peptides (Realini et al. FEBS Lett. 1994 348:109–113). Prokaryotic proteins do not normally contain PEST sequences because they do not have this enzymatic pathway.

However, a PEST-like sequence rich in the amino acids proline (P), glutamic acid (E), serine (S) and threonine (T) was recently identified at the amino terminus of LLO and demonstrated to be essential for *L. monocytogenes* pathogenicity (Decatur, A. L. and Portnoy, D. A. *Science* 2000 290:992–995). Decatur and Portnoy teach that the presence of this PEST-like sequence in LLO targets the protein for destruction by proteolytic machinery of the host cell so that once the LLO has served its function and facilitated the escape of *L. monocytogenes* from the phagolysosomal vacuole, it is destroyed before it can damage the cells.

It has now been found that the immune response to an antigen can be enhanced by fusion of the antigen to a non-hemolytic truncated form of listeriolysin O (ΔLLO). It is believed that the observed enhanced cell mediated immunity and anti-tumor immunity of the fusion protein results from the PEST-like sequence present in LLO which targets the antigen for processing.

SUMMARY OF THE INVENTION

An object of the present invention is to provide a method for enhancing the immunogenicity of an antigen which comprises fusing to the antigen a non-hemolytic truncated form of listeriolysin O (ΔLLO). In a preferred embodiment, the antigen is fused to a PEST-like amino acid sequence derived from *L. monocytogenes*.

Another object of the present invention is to provide compositions with enhanced cell mediated immunity and anti-tumor immunity which comprise an antigen fused to a PEST-like amino acid sequence derived from a prokaryotic organism.

Yet another object of the present invention is to provide a method for invoking an enhanced cell mediated or anti-tumor immunogenic response to an antigen in an animal comprising administering to the animal a composition comprising an antigen fused to a PEST-like amino acid sequence derived from a prokaryotic organism.

DETAILED DESCRIPTION OF THE INVENTION

Figure 1:
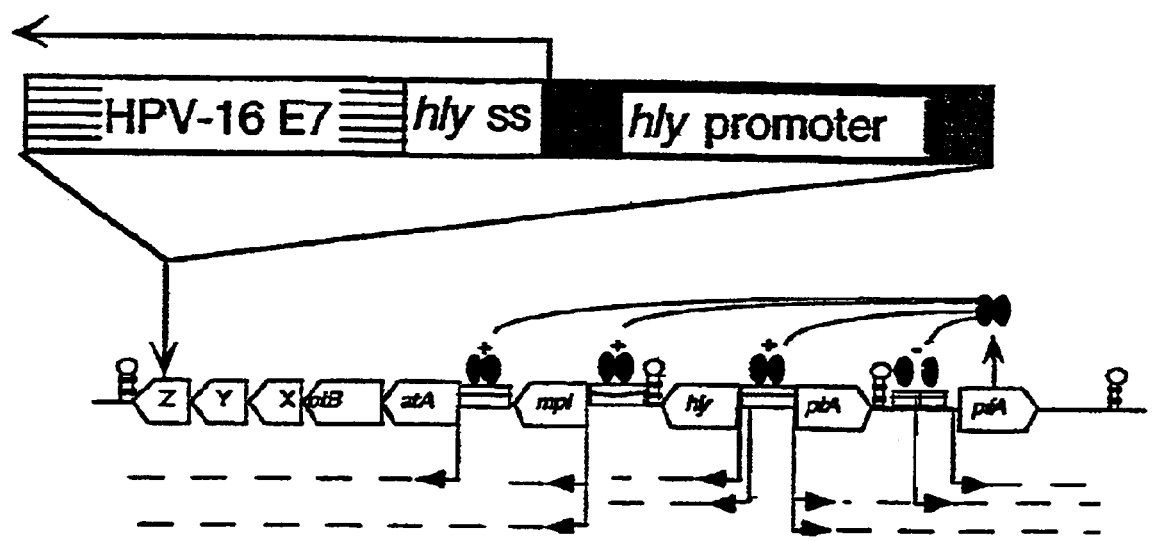
FIG. 1 is a diagram of an HPV-E7 chromosomal expression system constructed by integration of an E7 gene into the Listeria chromosome.

The present invention relates to a method for enhancing the immunogenicity of a selected antigen by fusion of the selected antigen to a non-hemolytic truncated form of listeriolysin O. It has now been found that fusion of an antigen to a non-hemolytic truncated form of listeriolysin O results in an antigen with enhanced immunogenicity as compared to antigen alone. This truncated form of listeriolysin O fused to an antigen better enables cell mediated immunity and anti-tumor immunity as compared to antigen alone. Further, these fusion proteins need not be expressed by *L. monocytogenes*, but rather can be expressed and isolated from other vectors and cell systems routinely used for protein expression and isolation.

Listeriolysin O (LLO) binds to cholesterol-containing membranes wherein it oligomerizes to form pores. The oligomerization is dependent on the presence of a reduced cystine residue at position 484 in the sequence that is required for oligomerization. The hly gene encodes a pro-protein of 529 residues (GenBank Accession No. P13128), the first 25 amino acids are the signal sequence and are cleaved from LLO when it is secreted by the bacterium. Thus, the full length active LLO protein is approximately 504 residues. For purposes of the present invention, by "truncated form of LLO or ΔLLO" it is meant a fragment of LLO which does not contain the activation domain at the amino terminus including cystine 484.

The present invention also relates to methods and compositions for enhancing cell mediated or anti-tumor immunity of a selected antigen by fusion of the selected antigen to a PEST-like amino acid sequence derived from a prokaryotic organism. For purposes of the present invention, by "PEST-like amino acid sequence" it is meant a peptide rich in the amino acids proline (P), glutamic acid (E), serine (S) and threonine (T). In a preferred embodiment the PEST-like amino acid sequence is derived from the amino acid terminus of Listeriolysin O (LLO), a hemolytic virulence factor of *L. monocytogenes*. In a more preferred embodiment, the PEST-like amino acid sequence comprises KENSISSMAP-PASPPASPKTPIEKKHADEIDK (SEQ ID NO:1).

Enhanced cell mediated immunity was demonstrated for fusion proteins comprising an antigen and truncated LLO containing the PEST-like amino acid sequence, SEQ ID NO:1. The ΔLLO used in these experiments was 416 amino acids long as 88 residues from the amino terminus which is inclusive of the activation domain containing cystine 484 were truncated. However, it is believed that other ΔLLOs without the activation domain, and in particular cystine 484, will also be effective. More particularly, it is believed that fusion of an antigen to any ΔLLO including the PEST-like amino acid sequence, SEQ ID NO:1, can enhance cell mediated and anti-tumor immunity of the antigen.

Enhanced immunogenicity of an antigen following fusion to a non-hemolytic truncated form of listeriolysin O was demonstrated. Specifically, experiments have been performed demonstrating that an *L. monocytogenes* vector that expresses and secretes a fusion product of Human Papilloma Virus (HPV) strain 16 E7 and listeriolysin, which comprises the PEST-like amino acid sequence SEQ ID NO:1, is a much more potent cancer immunotherapeutic for HPV immortalized tumors than a strain of *L. monocytogenes* that secretes the E7 protein alone. Experiments were also performed demonstrating that a recombinant vaccinia virus that carries the gene for the fusion protein LLO-E7 which contains the PEST-like amino acid sequence of SEQ ID NO:1 is a much more potent cancer immunotherapeutic for HPV immortalized tumors than an isogenic strain of vaccinia that carries the gene for E7 protein alone. In comparison, a short fusion protein Lm-AZ/-E7 comprising the E7 antigen fused to the promoter, signal sequence and the first 7 amino acid residues of LLO was an ineffective anti-tumor immunotherapeutic. This short fusion protein terminates directly before the PEST-like sequence and does not contain it.

In a first set of experiments, the HPV-E7 antigen was expressed in *L. monocytogenes*. An *L. monocytogenes* recombinant that expressed E7 was made by chromosomal integration of the E7 gene under the control of the hly promoter and with the inclusion of the hly signal sequence to ensure secretion of the gene product. The site of integration into the chromosome by homologous recombination was into a region that is non-essential for Lm virulence. The scheme for this is depicted in FIG. 1. The advantage in using this type of transformation is that resulting recombinants are stably transformed and contain no drug selection markers since the CAT gene, included in the plasmid to select for successful transformants after electroporation, is excised during a second recombination event. The expression and secretion of the antigen from the resulting recombinants, Lm-E7, was verified by Western Blot. In addition, therapeutic effects of Lm-E7 were optimized. For example, it was found that the best results were achieved delivering the vaccine orally as compared to parenterally and in a combined protection and regression mode that requires priming with Lm-E7 before tumor challenge and then administering Lm-E7 therapeutically after tumor challenge. Table 1 provides more details for optimized anti-tumor effects observed in this model in three different tumor cell lines, TC-1, C3 and EL-4/E7. Bacteria were delivered orally 14 and 7 days prior to tumor challenge and days 7 and 14 following tumor challenge. Delivery of $10^6$ bacteria intraperitoneally in a similar protocol provided no long-term protection. However, better protection was observed when Lm-E7 was delivered orally. More specifically, with this regimen approximately 50% of the animals remained tumor free in perpetuity and immunization seriously retarded tumor growth in all animals.

TABLE 1

Treatment with Lm-E7

| Treatment | Number of tumor free animals versus total in study (number survived) | | |
|---|---|---|---|
| | $10^5$ TC-1 on day 60 | $10^6$ C3 on day 42 | $5 \times 10^5$ EL-4/E7 on day 40 |
| $10^8$ Lm-E7 | 3/8 (5) | 4/8 (8) | 4/8 (6) |
| $10^8$ Lm-Gag (ZY-18) | 2/8 (2) | 0/8 (0) | 2/8 (0) |
| Naive | 0/8 (0) | 0/8 (0) | 1/8 (0) |

Animals administered TC-1 or EL-4/E7 tumor cells that were tumor free were re-challenged on day 60 with TC-1 or day 40 EL-4/E7, respectively. The two animals in each group that had been immunized with Lm-Gag grew tumors whereas the animals immunized with Lm-E7 remained tumor free until termination of the experiment (day 124 in the case of TC-1 and day 54 for EL-4/E7).

Compared to results previously disclosed with Lm-NP and the RENCA, CT-26 and B16F10-NP models (Pan et al. 1995), the Lm-E7 was less effective than expected. Accordingly, an Lm-E7 construct was prepared in accordance with the method taught for preparation of the Lm-NP construct of Pan et al. (*Cancer Res.* 1995 55:4776–4779).

Figure 2:
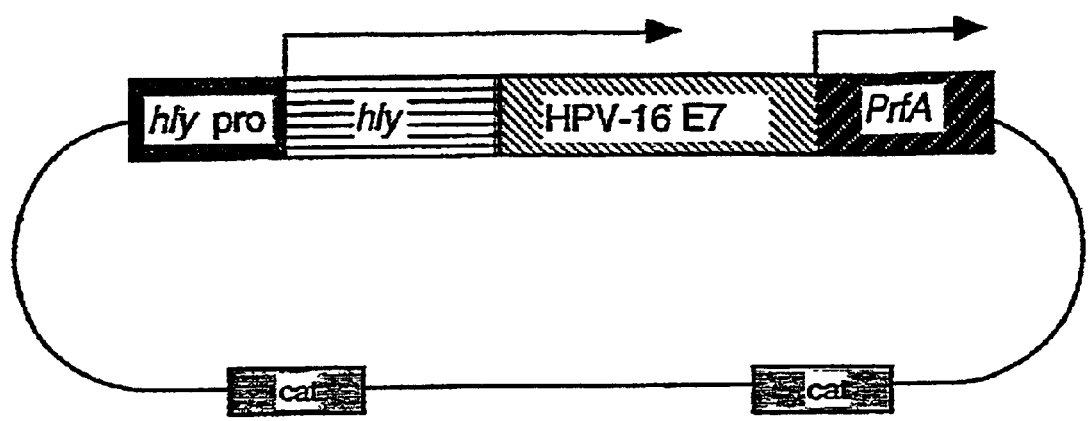
FIG. 2 is a diagram of a preferred multi-copy plasmid containing prfA and E7 fused to a truncated form of the hly gene (Δhyl) that produced ΔLLO.

Specifically, a second *L. monocytogenes* vaccine that expresses a E7 fusion protein, referred to as Lm-LLO-E7, was prepared by complementing a prfA-deletion mutant with a plasmid containing a copy of the prfA gene and a copy of the E7 gene fused to a form of the hly gene truncated to eliminate the hemolytic activity of the enzyme, ΔLLO (see FIG. 2). Functional LLO is maintained by the organism via the endogenous chromosomal copy of hly. The expression and secretion of the fusion protein was verified by Western blot.

The ability of the Lm-LLO-E7 and Lm-E7 vaccine to induce anti-tumor immunity was then compared in a regression model. As shown in Table 2, Lm-LLO-E7 was found to be more effective than Lm-E7. This difference in efficacy is believed to be due to the presence of the PEST-like sequence, SEQ ID NO:1, in Lm-LLO-E7.

TABLE 2

Number of mice cured of TC-1 tumor at conclusion of experiment

| Treatment | Mice TC-1 free at day 45 | Mice alive at day 45 | Mice alive at day 134 |
|---|---|---|---|
| Naive | 0/8 | 0/8 | 0/8 |
| Lm-LLO-E7 | 4/8 | 8/8 | 4/8 |
| Lm-E7 | 0/8 | 7/8 | 0/8 |

Thus, expression of the foreign gene as a fusion protein with ΔLLO enhances the immunogenicity of the antigen.

Figure 3:
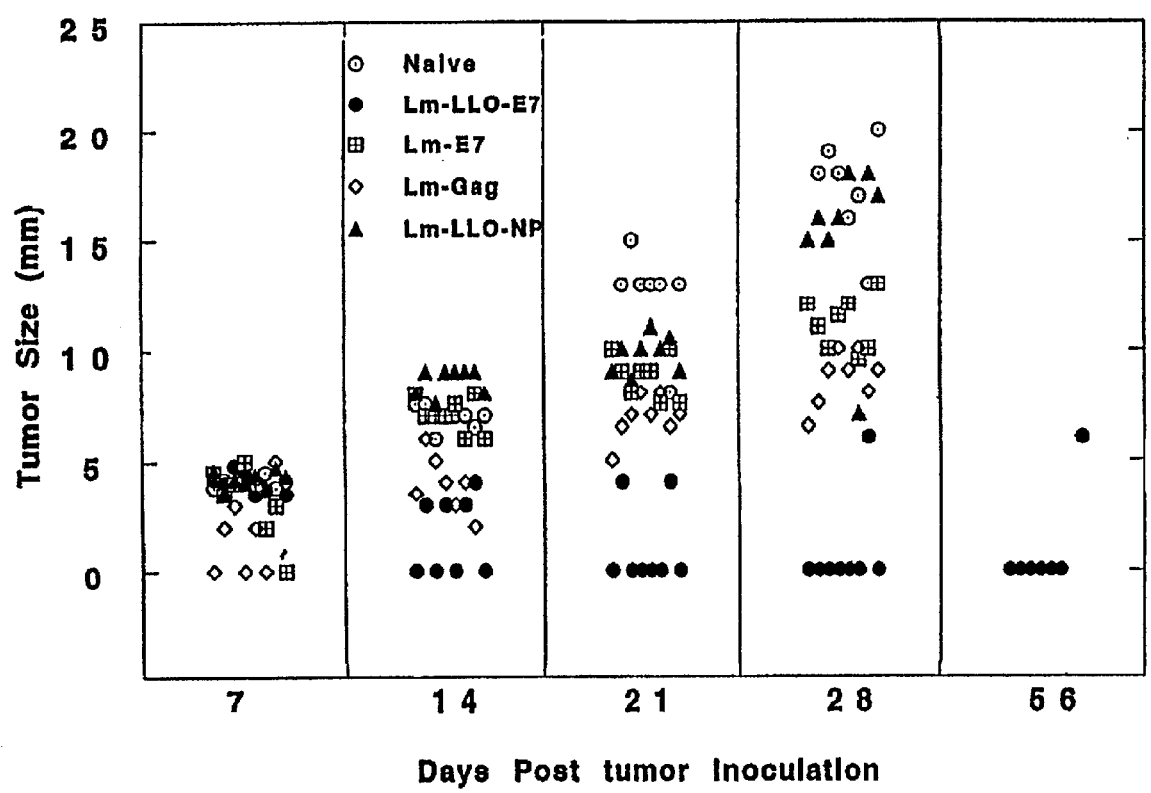
FIG. 3 is a graph showing tumor immunotherapeutic efficacy of E7 antigen expressed in *L. monocytogenes*. Tumor size in millimeters in mice is shown at 7, 14, 21, 28 and 56 days post tumor-inoculation. Naive mice are depicted by an open-circle; mice administered Lm-LLO-E7 are depicted by a filled circle; mice administered Lm-E7 are depicted by a square; mice administered Lm-Gag are depicted by an open diamond; and mice administered Lm-LLO-NP are depicted by a filled triangle.

Additional experiments were performed to compare the ability of Lm-E7 with Lm-LLO-E7 to induce the regression of established sub-cutaneous HPV-16 immortalized tumors from C57Bl/6 mice. Results from these experiments are depicted in FIG. 3. In these experiments, mice were immunized i.p. with 0.1 $LD_{50}$ with one of four constructs, Lm-E7, Lm-Gag (isogenic with Lm-E7 except for the antigen expressed), Lm-LLO-E7 or Lm-LLO-NP. Lm-LLO-NP is isogenic with Lm-LLO-E7 but expresses influenza antigen. A second immunization was performed on day 14. As can be seen in FIG. 3, 6 of 8 mice immunized with Lm-LLO-E7 were cured of their tumors and remained tumor free. None of the other animals showed any regression of the established tumors. Similar results have been achieved for Lm-LLO-E7 under different immunization protocols. Further, just one immunization has been demonstrated to cure mice of established TC-1 of 5 mm diameter.

Figure 4:
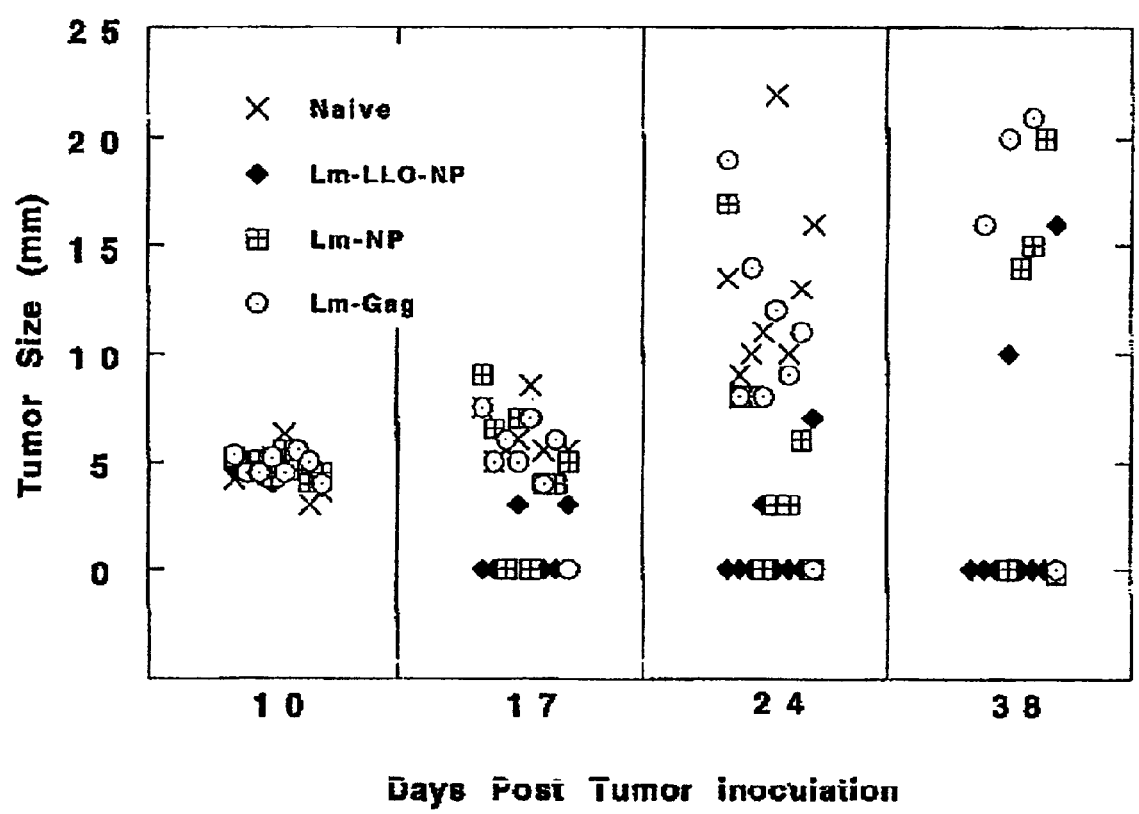
FIG. 4 is a graph showing tumor immunotherapeutic efficacy of NP antigen expressed in *L. monocytogenes*. Tumor size in millimeters in mice is shown at 10, 17, 24, and 38 days post tumor-inoculation. Naive mice are depicted by an X; mice administered Lm-LLO-NP are depicted by a filled diamond; mice administered Lm-NP are depicted by a square; and mice administered Lm-Gag are depicted by an open circle.

In order to confirm the generality of the finding that fusing LLO to an antigen confers enhanced immunity, a version of Lm-NP similar to Lm-E7 was constructed. This recombinant was prepared as shown in FIG. 1 except that influenza nucleoprotein replaced E7 as the antigen. The ability of the new Lm-NP was compared with Lm-LLO-NP (described in U.S. Pat. No. 5,830,702 and prepared as shown in FIG. 2). Results from these experiments are shown in FIG. 4. In these experiments, 32 BALB/c mice were inoculated with $5 \times 10^5$ RENCA-NP tumor cells. RENCA-NP is a renal cell carcinoma retrovirally transduced with influenza nucleoprotein NP (described in U.S. Pat. No. 5,830,702). After palpable macroscopic tumors had grown on day 10, eight animals in each group were immunized i.p. with $0.1 LD_{50}$ with one of three constructs, Lm-NP, Lm-Gag (isogenic with Lm-NP except for the antigen expressed) and Lm-LLO-NP. The animals received a second immunization one week later. Eight animals were left untreated. At the end of the experiment on day 40, all the mice in the naive group had large tumors or had died. Only one mouse in the group that received Lm-Gag and two mice in the group that received Lm-NP were tumor free. This experiment shows that fusing an antigen to LLO is not restricted to E7 and suggests that the form of the antigen is not important.

Additional experiments were performed to confirm the enhanced therapeutic efficacy of a fusion protein comprising the E7 antigen and a truncated form of listeriolysin O. In these experiments a vaccinia vector that expresses E7 as a fusion protein with a non-hemolytic truncated form of listeriolysin O was constructed. The WR strain of vaccinia was used as the recipient and the fusion gene was excised from the listerial plasmid and inserted into pSC11 under the control of the p75 promoter. This vector was chosen because it is the transfer vector used for the vaccinia constructs Vac-SigE7Lamp and Vac-E7 and would therefore allow direct comparison with Vac-LLO-E7. In this way all three vaccinia recombinants would be expressed under control of the same early/late compound promoter p7.5. In addition SC11 allows the selection of recombinant viral plagues to TK selection and β-galactosidase screening.

Figure 5:
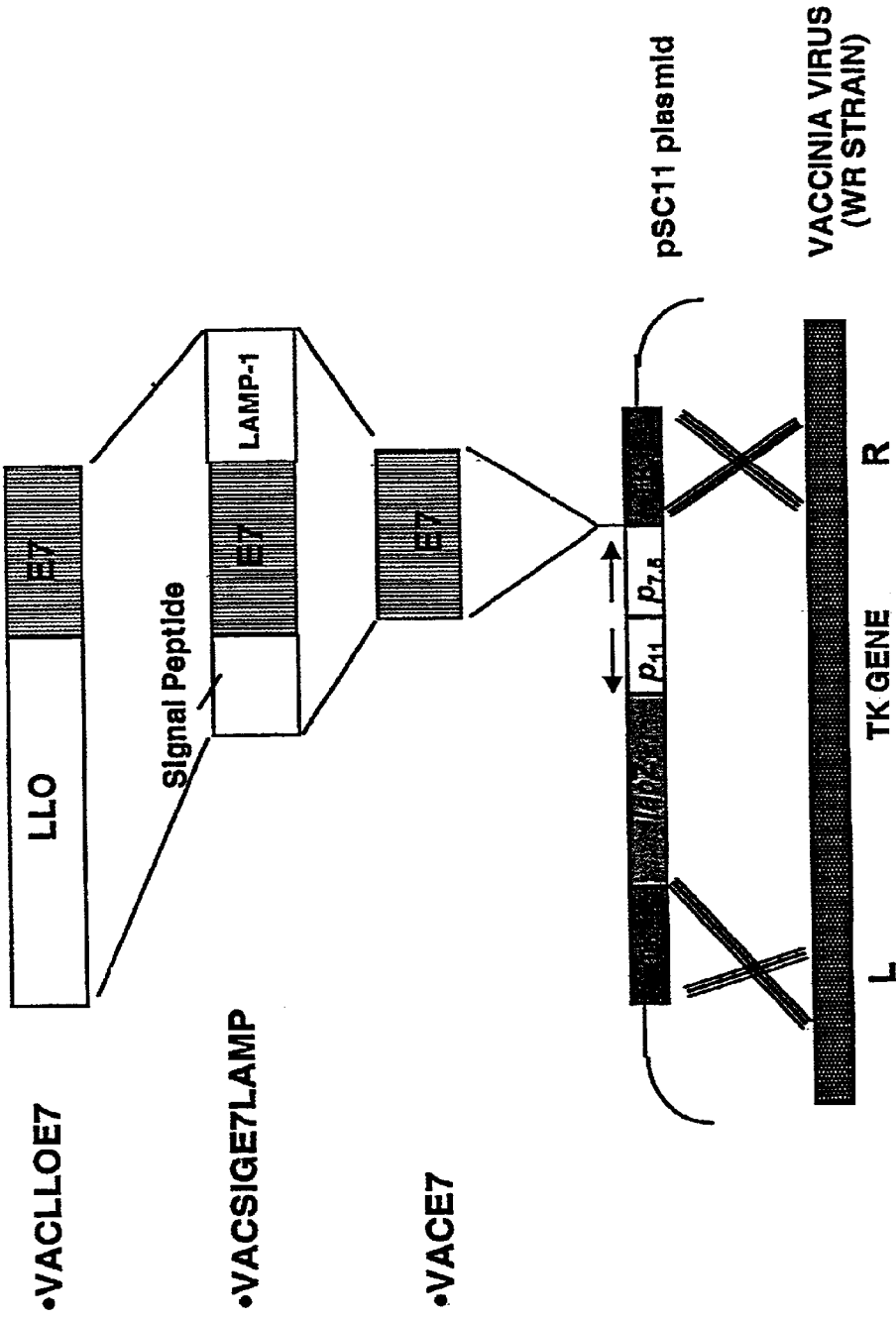
FIG. 5 is a diagram of various Vaccinia virus constructs expressing different forms of HPV16 E7 protein.

FIG. 5 shows the various vaccinia constructs used in these experiments. Vac-SigE7Lamp is a recombinant vaccinia virus that expressed the E7 protein fused between lysosomal associated membrane protein (LAMP-1) signal sequence and sequence from the cytoplasmic tail of LAMP-1 (Lin et al. *Proc. Natl. Acad. Sci. USA* 1995 92:11671–5; Wu et al. *Cancer Res.* 1996 56:21–6). It was designed to facilitate the targeting of the antigen to the MHC class II pathway.

The following modifications were made to allow expression of the gene product by vaccinia: (a) the T5XT sequence that prevents early transcription by vaccinia was removed from the 5' portion of the LLO-E7 sequence by PCR; and (b) an additional XmaI restriction site was introduced by PCR to allow the final insertion of LLO-E7 into SC11. Successful introduction of these changes (without loss of the original sequence that encodes for LLO-E7) was verified by sequencing. The resultant pSC11-E7 construct was used to transfect the TK-ve cell line CV1 that had been infected with the wildtype vaccinia strain, WR. Cell lysates obtained from this co-infection/transfection step contain vaccinia recombinants that were plaque purified 3 times. Expression of the LLO-E7 fusion product by plaque purified vaccinia was verified by Western blot using an antibody directed against the LLO protein sequence. In addition, the ability of Vac-LLO-E7 to produce CD8+ T cells specific to LLO and E7 was determined using the LLO(91–99) and E7(49–57) epitopes of Balb/c and C57/BL6 mice, respectively. Results were confirmed in a chromium release assay.

Figure 6:
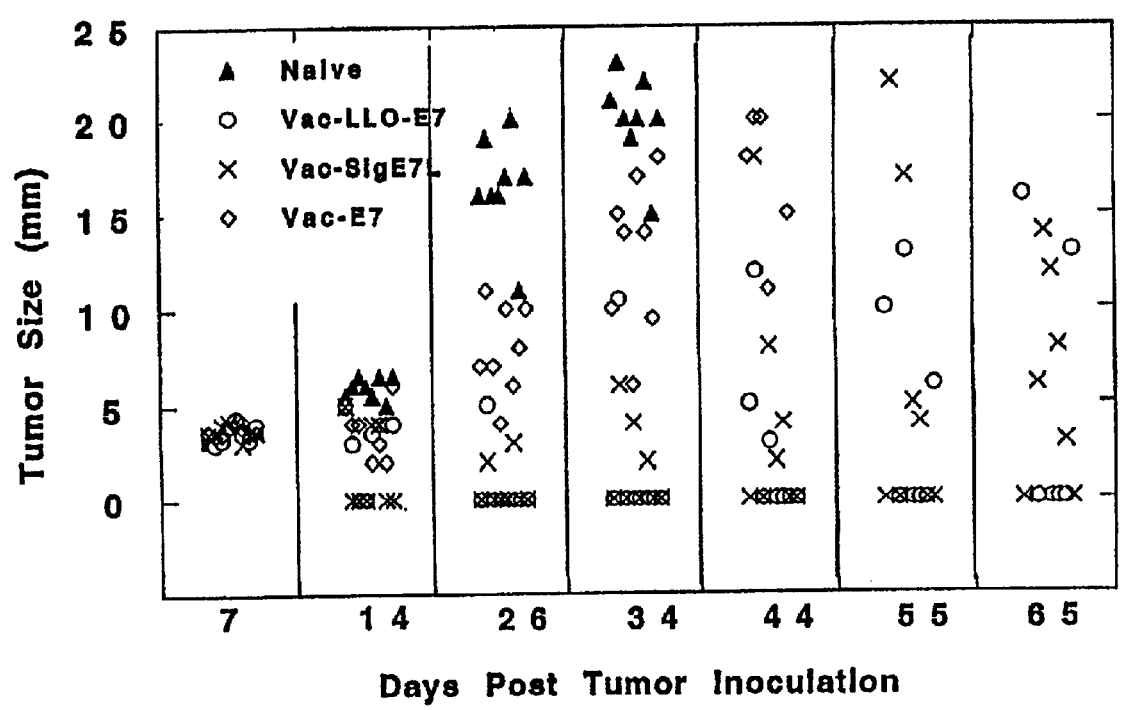
FIG. 6 is a graph showing tumor immunotherapeutic efficacy of antigens expressed by Vaccinia. Tumor size in millimeters in mice is shown at 7, 14, 26, 34, 44, 55 and 65 days post tumor-inoculation. Naive mice are depicted by a filled triangle; mice administered Vac-LLO-E7 are depicted by an open circle; mice administered Vac-SigE7L are depicted by an X; and mice administered Vac-E7 are depicted by an open diamond.

Tumor rejection studies were performed with TC-1 following the same protocol as described supra. Two experiments were performed with differing delays before treatment was started. In one experiment, treatments were initiated when the tumors were about 3 mm in diameter (see FIG. 6). As of day 76, 50% of the Vac-LLO-E7 treated mice are tumor free and 25% of the Vac-SigE7Lamp mice are tumor free.

In the second experiment, TC-1 tumors were grown to a larger size (5 to 6 mm). The LLO-E7 fusion protein based vectors were then compared against a larger number of vectors. Although some of the vaccine groups showed significant temporary regression of TC-1, by day 65 the data clearly shows that Lm-LLO-E7 and Vac-LLO-E7 are the most effective vaccines with respect to the ability to permanently induce the regression of established TC-1. Only 12% of the Vac-SigE7Lamp treated mice were tumor free while 37% of the Vac-LLO-E7 and Lm-LLO-E7 mice were tumor free. All other mice were dead.

Thus, expression of the antigen as a fusion protein with a non-hemolytic truncated form of listeriolysin O in host cell systems in listeria and host cell systems other than listeria results in enhanced immunogenicity of the antigen. While comparative experiments were performed with vaccinia, a multitude of other plasmids and expression systems which can be used to express these fusion proteins are known. For example, bacterial vectors useful in the present invention include, but are not limited to Salmonella sp., Shigela sp., BCG, *L. monocytogenes* and *S. gordonii*. In addition the fusion proteins can be delivered by recombinant bacterial vectors modified to escape phagolysosomal fusion and live in the cytoplasm of the cell. Viral vectors useful in the present invention include, but are not limited to, Vaccinia, Avipox, Adenovirus, AAV, Vaccinia virus NYVAC, Modified vaccinia strain Ankara (MVA), Semliki Forest virus, Venezuelan equine encephalitis virus, herpes viruses, and retroviruses. Naked DNA vectors can also be used.

Accordingly, the present invention provides methods for enhancing the immunogenicity of an antigen via fusion of the antigen to a non-hemolytic truncated form of listeriolysin O or ΔLLO. In a preferred embodiment, the antigen is fused to the PEST-like amino acid sequence, SEQ ID NO:1, of LLO.

The present invention also provides methods for enhancing cell mediated and anti-tumor immunity and compositions with enhanced immunogenicity which comprise a PEST-like amino acid sequence derived from a prokaryotic organism fused to or embedded within an antigen. The PEST-like sequence can be fused to either the amino terminus or the carboxy terminus of the antigen. As demonstrated herein, fusion of an antigen to the PEST-like sequence of *L. monocytogenes* enhanced cell mediated and anti-tumor immunity of the antigen. It is believed that fusion of an antigen to other PEST-like sequences derived from other prokaryotic organisms will also enhance immunogenicity of the antigen. PEST-like sequence of other prokaryotic organism can be identified routinely in accordance with methods such as described by Rechsteiner and Roberts (TBS 21:267–271,1996) for *L. monocytogenes*. Alternatively, PEST-like amino acid sequences from other prokaryotic organisms can also be identified based by this method. Other prokaryotic organisms wherein PEST-like amino acid sequences would be expected to include, but are not limited to, other Listeria species. For example, the *L. monocytogenes* protein ActA contains four such sequences. These are KTEEQPSEVNTGPR (SEQ ID NO:2), KASVTDTSEG-DLDSSMQSADESTPQPLK (SEQ ID NO:3), KNEEVNASDFPPPPTDEELR (SEQ ID NO:4), and RGGIPTSEEFSSLNSGDFTDDENSETTEEEIDR (SEQ ID NO:5). Also Streptolysin O from Streptococcus sp. contain a PEST-LIKE sequence. For example, *Streptococcus pyogenes* Streptolysin O comprises the PEST-like sequence KQNTASTETTTTNEQPK (SEQ ID NO:6) at amino acids 35–51 and *Streptococcus equisimilis* Streptolysin O comprises the PEST-like sequence KQNTANTETTTTNEQPK (SEQ ID NO:7) at amino acids 38–54. Further, it is believed that the PEST-like sequence can be embedded within the antigenic protein. Thus, for purposes of the present invention, by "fusion" it is meant that the antigenic protein comprises both the antigen and the PEST-like amino acid sequence either linked at one end of the antigen or embedded within the antigen.

In a preferred embodiment, fusion proteins of the present invention are produced recombinantly via a plasmid which encodes either a truncated form of the listeriolysin O comprising the PEST-like amino acid sequence of *L. monocytogenes* or a PEST-like amino acid sequence derived from another prokaryotic organism and the antigen. However, the antigen may also be chemically conjugated to the truncated form of listeriolysin O comprising the PEST-like amino acid sequence of *L. monocytogenes* or a PEST-like amino acid sequence derived from another prokaryotic organism. For purposes of the present invention, by "antigen" it is meant to include the native antigen gene or gene product or truncated versions of these that include identified T cell epitopes. These fusion proteins can then be incorporated into vaccines for administration to animals, preferably humans, to invoke an enhanced immune response against the antigen of the fusion protein. In one embodiment, the fusion proteins of the present invention are delivered as DNA vaccines, RNA vaccines or replicating RNA vaccines. As will be obvious to those of skill in the art upon this disclosure, vaccines comprising the fusion proteins of the present invention are particularly useful in the prevention and treatment of infectious and neoplastic diseases.

These vaccines may further comprise adjuvants. Examples of adjuvants useful in these vaccines include, but are not limited to, unmethylated CpG, quill glycosides, CFA, QS21, monophosphoryl lipid A, liposomes, and bacterial mitogens and toxins.

The following examples are provided for illustrative purposes only and are not intended to limit the invention.

EXAMPLES

Example 1

Tumor Cell Lines

TC-1 is a lung epithelial cell from C57BL/6 mice immortalized by HPV-16 E6 and E7 and transformed by pVEJB expressing activated human c-HA-ras. C3 is a mouse embryo cell frp, C57BL/6 mice immortalized with the complete genome of HPV16 and transformed with pEJ-ras. EL-4/E7 is the thymoma EL-4 retrovirally transduced with E7.

Example 2

Comparison of Efficacy of Lm-GG/E7, Lm-AZ/E7 and Vac-SigE7Lamp

TC-1 ($1 \times 10^5$) or C-3 ($5 \times 10$)$^5$ tumor cells were implanted subcutaneously in mice and allowed to grow for 7 to 9 days by which time they were palpable (~5 mm in size). Mice were then immunized i.p. with one of three constructs, Vac-SigE7Lamp ($10^7$ PFU), Lm-E7 ($10^6$ CFU) or Lm-LLO-E7 ($10^7$ CFU). Animals received Lm-LLO-E7 and LM-E7 on days 7 and 14. Surviving mice were re-challenged with $10^5$ TC-1 on day 43.

Example 3

Comparison of Efficacy of Vac-LLO-E7, Vac-E7 and Vac-SigE7Lamp

Four groups of 8 mice were implanted with $10^5$ cells of TC-1. After 7 days the tumors were approximately 4 mm in size. One group of mice was untreated. Each of the other groups received $10^7$ PFU of either Vac-E7, Vac-LLO-E7 or Vac-Sig-E7-lamp 7. A booster dose was administered on day 14.

Example 4

Comparison of Efficacy of Vac-LLO-E7 and Lm-LLO-E7 with Various Other Vectors

TC-1 tumor cells ($2 \times 10^5$) were implanted s.c. on the left flank in 96 C57BL/6 mice and allowed to grow for 7 days. The mice were divided into groups of 8 mice and each group was treated with one of the following vaccine: naive (no vaccine); Vac SigE7Lamp, $10^7$ PFU, i.p.; Vac-LLO-E7, $10^7$ PFU, i.p.; or Lm-LLO-E7, $10^7$ PFU, i.p. The animals received a booster immunization one week later. Tumor growth was followed every two days by caliper measurement and recorded as the average of the narrowest and longest surface length. Immune parameters were also determined.

Example 5

Construction of Lm-LLOPEST-E7

The LLO-PEST-E7 fragment can be constructed via SOEing PCR.

In Step 1 of this method, PCR reaction 1 uses primer pair GG-36/GG-78 or GG-77/AZ-9 with pGG-55 for the template. PCR reaction 2 uses LLO-PEST and E7 products from the first reaction as templates and the primers GG-36 and AZ-9.

GG-36: 5'-GCTAGCCCTCCTTTGATTAGTATATTC-3' (SEQ ID NO:8)
GG-77: 5'-GCGGATGAAATCGATAAGCATGGAGAT ACACCTACA-3' (SEQ ID NO:9)
GG-78: 3'-CGCCTACTTTAGCTATTCGTACCTCTAT GTGGATGT-5' (SEQ ID NO:10)
AZ-9: 3'-GAGTCTTTGGTATTGGGCCC-5' (SEQ ID NO:11)

In step 2, the final SOEing PCR product of 0.7 Kb is ligated into the TA vector pCR2.1.

In step 3, the LLO-PEST-E7 is digested from the plasmid with the enzyme NheI for 2 hours followed by ethanol precipitation and the enzyme XmaI overnight. The prfA fragment from pGG-49 is digested with the enzyme SalI for 2 hours followed by ethanol precipatation and XmaI overnight. pDP-2028 is digested with SalI and XbaI for 2 hours followed by ethanol precipitation and resuspension in Tris:EDTA (TE). The fragment can be stored overnight at 4° C.

In step 4, the 0.7 Kb LLO-PEST-E7, 1.0 Kb prfA and the 9.7 Kb plasmid are ligated. This plasmid is then used to transform XFL-7. Secretion of a 15 Kb fragment can be verified via Western blot. Efficacy is verified against TC-1 tumors.

Alternatively, a chromosomal integrant can be generated by amplifying the LLO-PEST-E7 fragment using the primer AZ-B (5'-GCTCTAGATTATGGTTTCTGAG-3'; SEQ ID NO:12) to install a 3' XbaI site and primer ZY-3 (5'-GGGGTACCCTCCTTTGATTAGTATAT-3'; SEQ ID NO:13) to install a 5' KpnI site. pZY-37 and the LLO-PEST-E7 fragment are digested with KpnI and XbaI separately or in NEB buffer 2+ BSA overnight. The fragment is ligated into pZY-37 and the following protocol for chromosomal integration is followed. Secretion and efficacy are verified as described above.

What is claimed is:

1. A method for enhancing the immunogenicity of an antigen comprising fusing to the antigen a PEST-like amino acid sequence derived from a prokaryotic organism, wherein the antigen is selected from the group consisting of TC-1 cell antigen, human papilloma virus E7, and influenza virus NP, the PEST-like amino acid sequence is selected from the group consisting of SEQ ID NOS:1–7, and the prokaryotic organism is selected from the group consisting of *Listeria monocylogenes* and Streptococcus species.

2. The method of claim 1 where the PEST-like amino acid sequence derived from a prokaryotic organism consists of SEQ ID NO:1.

3. The method of claim 1 wherein the PEST-like amino acid sequence derived from a prokaryotic organism is fused to the antigen by recombinant expression of a plasmid encoding the PEST-like amino acid sequence derived from a prokaryotic organism and the antigen.

4. A method for invoking an enhanced cell mediated or anti-tumor immunogenic response to an antigen in an animal, the method comprising administering to the animal a composition comprising an antigen and a PEST-like amino acid sequence, derived from a prokaryotic organism, said PEST-like amino acid sequence being fused to or embedded within said antigen, wherein the antigen is selected from the group consisting of TC-1 cell antigen, human papilloma virus E7, and influenza virus NP, the PEST-like amino acid sequence is selected from the group consisting of SEQ ID NOS:1–7, and the prokaryotic organism is selected from the group consisting of Listeria monocylogenes and Streptococcus species.

* * * * *